United States Patent
Kang

(10) Patent No.: US 10,409,954 B2
(45) Date of Patent: Sep. 10, 2019

(54) TERMINAL AND METHOD FOR PROVIDING HEALTH CONTENTS

(71) Applicant: SAMSUNG ELECTRONICS CO., LTD., Suwon-si (KR)

(72) Inventor: Seok-Myong Kang, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 964 days.

(21) Appl. No.: 14/455,548

(22) Filed: Aug. 8, 2014

(65) Prior Publication Data

US 2015/0046179 A1 Feb. 12, 2015

(30) Foreign Application Priority Data

Aug. 8, 2013 (KR) .................. 10-2013-0094210

(51) Int. Cl.
*G06F 19/00* (2018.01)

(52) U.S. Cl.
CPC .................. *G06F 19/3418* (2013.01)

(58) Field of Classification Search
None
See application file for complete search history.

(56) References Cited

U.S. PATENT DOCUMENTS

| | | | | |
|---|---|---|---|---|
| 2003/0130595 A1* | 7/2003 | Mault | .................. | G06F 19/3418 600/567 |
| 2006/0136173 A1* | 6/2006 | Case, Jr. | .................. | A63B 24/00 702/182 |
| 2007/0142179 A1* | 6/2007 | Terao | .................. | A63B 21/0056 482/8 |
| 2008/0058740 A1* | 3/2008 | Sullivan | .................. | A61F 13/42 604/361 |
| 2008/0096726 A1* | 4/2008 | Riley | .................. | A63B 24/0006 482/8 |
| 2012/0095302 A1 | 4/2012 | Adhikari | | |
| 2013/0095459 A1* | 4/2013 | Tran | .................. | A61B 5/6816 434/247 |
| 2013/0268292 A1* | 10/2013 | Kim | .................. | G16H 20/10 705/2 |
| 2014/0122702 A1* | 5/2014 | Jung | .................. | H04L 43/0876 709/224 |
| 2014/0275852 A1* | 9/2014 | Hong | .................. | A61B 5/02427 600/301 |
| 2014/0278220 A1* | 9/2014 | Yuen | .................. | G01B 21/16 702/150 |

FOREIGN PATENT DOCUMENTS

| | | |
|---|---|---|
| JP | 2008-262504 A | 10/2008 |
| KR | 10-2012-0075629 A | 7/2012 |
| KR | 10-2012-0079768 A | 7/2012 |

OTHER PUBLICATIONS

Sokolowski, Peter, "Ask the Editor 'cleanliness' and 'cleanness'" Jul. 16, 2009.*

* cited by examiner

*Primary Examiner* — Neal Sereboff
(74) *Attorney, Agent, or Firm* — Sughrue Mion, PLLC

(57) ABSTRACT

The present disclosure relates to a terminal, and more particularly to a terminal and a method for providing health content. A method of providing health content using health information, includes receiving at least one piece of health information, comparing the received at least one piece of health information with a threshold value, and providing health content for a user to lessen a difference between the at least one piece of health information and the threshold value.

9 Claims, 3 Drawing Sheets

TERMINAL AND METHOD FOR PROVIDING HEALTH CONTENTS

CROSS-REFERENCE TO RELATED APPLICATIONS

This application claims priority from Korean Patent Application No. 10-2013-0094210, which was filed in the Korean Intellectual Property Office on Aug. 8, 2013, the disclosure of which is incorporated herein by reference in its entirety.

BACKGROUND

1. Technical Field

Apparatuses and methods consistent with exemplary embodiments relate to a terminal, and more particularly to a terminal and a method for providing health content.

2. Description of the Related Art

As ultra-high speed Internet services have gained wider access and next-generation televisions (TVs) that have operating systems (OSs) and central processing units (CPUs) have become more prolific, the variety of services and applications that are provided has increased in number. Additionally, demands on mobile phones and smart TVs, through which videos can be watched while providing the functions of a PC and a TV, are rapidly increasing. For example, through terminals such as smart TVs, various services such as connecting to the Internet and reproducing videos can be performed as well as medical services that are required in relation to health.

However, the user is tasked with inputting his or her body temperature, blood pressure, and a pulse on his or her own. There does not exist an application or a program for adaptively managing the health of the user. Accordingly, if a user is seeking medical service offerings, including, for example, suitable content according to a difference between an indoor environment and an outdoor environment corresponding to a current health state of the user. Further, in view of the development of healthcare technology in which medicines and IT technology are combined, terminals such as TVs could provide the users with health management services and medical services without the restriction of time and space, for example, through communications with various devices, such as blood pressure monitors and blood glucose meters.

SUMMARY

As described above, there is a need to measure the body information of a user or receive a value measured by a separate measurement unit in order to be able to provide helpful content to manage the health of the user to the user, or to analyze an indoor environment and calculate a difference between the measured indoor environment and the outdoor environment in order to provide content that is helpful for managing the health of the user.

Accordingly, the present disclosure provides a terminal and a method for providing health content.

The present disclosure also provides content helpful to management of health in association with various measurement units, such as a blood pressure monitor or a blood glucose meter, for checking the health of the user.

The present disclosure also provides content helpful to management of health according to a difference between an indoor temperature and an outdoor temperature, and monitors a health environment of the user.

In accordance with an aspect of an exemplary embodiment, there is provided a method of providing health content using health information, the method including receiving at least one piece of health information, comparing the received at least one piece of health information with a threshold value, and providing health content for a user to lessen a difference between the at least one piece of health information and the threshold value.

The method may further include outputting the health content to at least one of a display and a speaker.

The health content may include information for adjusting a body information value of the user included in the at least one piece of health information toward the threshold value.

The threshold value may be a standard threshold value corresponding to a standard body shape.

The body information value may include at least one of a blood pressure value, a blood sugar value, a pulse value, a human body fat value, a weight value, an organic composite substance value due to at least one of atopy, asthma, stress, and exhalation, and a height value of the user.

The providing of the health content may include outputting health content including a method of adjusting the health information to reach the threshold value.

The health content may include at least one of an exercise method, a diet therapy, a game, a recommend sleeping time, ventilation, recommendation of a hospital, and a difference between threshold values.

The method may further include transmitting a control signal to at least one of an air conditioner, a humidifier, and an air cleaner for a period of time set by the user for controlling at least one of temperature, humidity, and cleanness according to a difference between an indoor environment information value and a corresponding environment information threshold value.

According to an aspect of another exemplary embodiment, there is provided a health content providing method including receiving indoor environment information and outdoor environment information, comparing the indoor environment information with the outdoor environment information and generating comparison results, and outputting health content for a user according to the comparison results.

The output health content may include information for lessening a difference between the indoor environment information and the outdoor environment information.

The information that may be provided may be configured such that the user adapts to the outdoor environment information.

The indoor environment information may be received from a gateway existing in an interior where at least one of a temperature, a humidity, an ultraviolet ray index, and a cleanness may be measured.

The outdoor environment information may be received in response to a request to a server, and may include at least one of a temperature, a humidity, an ultraviolet ray index, and a cleanness.

The health content may be output to at least one of a display and a speaker.

The method may further include receiving standard threshold values for temperature, humidity, ultraviolet ray index, and cleanliness to compare the indoor environment information with the outdoor environment information.

Comparing of the indoor environment information and the outdoor environment information further may include comparing at least two of the indoor environment information, the outdoor environment information, and the received standard threshold value.

The outputting of the health content further may include transmitting the health content to a terminal of the user.

According to an aspect of an exemplary embodiment, there is provided a terminal for providing health content, the terminal including a receiver configured to receive at least one of outdoor environment information and at least one piece of health information, a controller configured to control comparing of the at least one of outdoor environment information and at least one piece of health information with a threshold value, and control providing of health content for the user to lessen a difference between the at least one of outdoor environment information and at least one piece of health information and the threshold value, and a display configured to display the health content.

The terminal may further include a measurement unit configured to measure an indoor environment information by measuring at least one of a temperature, a humidity, an ultraviolet ray index, and a cleanness.

The terminal may further include a communication unit configured to transmit the health content to at least one of a portable terminal, a gateway, a body information measurement unit, and a server of the user.

The terminal may further include a camera configured to detect a movement of the user.

The controller may be further configured to calculate a calorie consumed through the movement of the user.

The terminal may further include a storage configured to store the at least one piece of health information, the outdoor environment information, indoor environment information, and comparison result.

The storage may be further configured to store at least one of an exercise method, a diet therapy, a game, a recommend sleeping time, ventilation, recommendation of a hospital, and a difference between threshold values for a blood pressure value, a blood sugar value, a pulse value, a human body fat value, a weight value, an organic composite substance value due to at least one of atopy, asthma, stress, and exhalation, and a height value of the user included in the health information to generate health content.

The storage may be further configured to store information that recommends at least one of wearing of clothes, a sunscreen agent, ultraviolet ray shielding glasses, and a mask, and an additional function by which at least one of temperature, humidity, ultraviolet ray index, and cleanliness included in indoor environment information reaches at least one of temperature, humidity, ultraviolet ray index, and cleanliness to generate health content.

The health content may include at least one of information for adjusting a body information value of the user included in the at least one piece of health information toward the threshold value, and information for lessening the difference between the measured indoor environment information and the outdoor environment information.

The controller may be further configured to transmit a control signal to at least one of an air conditioner, a humidifier, and an air cleaner for a period of time set by the user for controlling at least one of a temperature, a humidity, and a cleanliness according to a difference between an indoor environment value and a corresponding environment threshold value.

The threshold values may be standard threshold values set to different values for a blood pressure value, a blood sugar value, a pulse value, a human body fat value, a weight value, an organic composite substance value due to at least one of atopy, asthma, stress, and exhalation, and a height value of the user included in the health information, and a temperature, a humidity, an ultraviolet ray index, and a cleanliness included in the outdoor environment information.

The controller may be further configured to compare at least two of the health information, the outdoor environment information, and the threshold value.

BRIEF DESCRIPTION OF THE DRAWINGS

The above and/or other aspects, features, and advantages of the present disclosure will become apparent and more readily appreciated from the following detailed description of exemplary embodiments, taken in conjunction with the accompanying drawings, in which.

DETAILED DESCRIPTION

Figure 1:
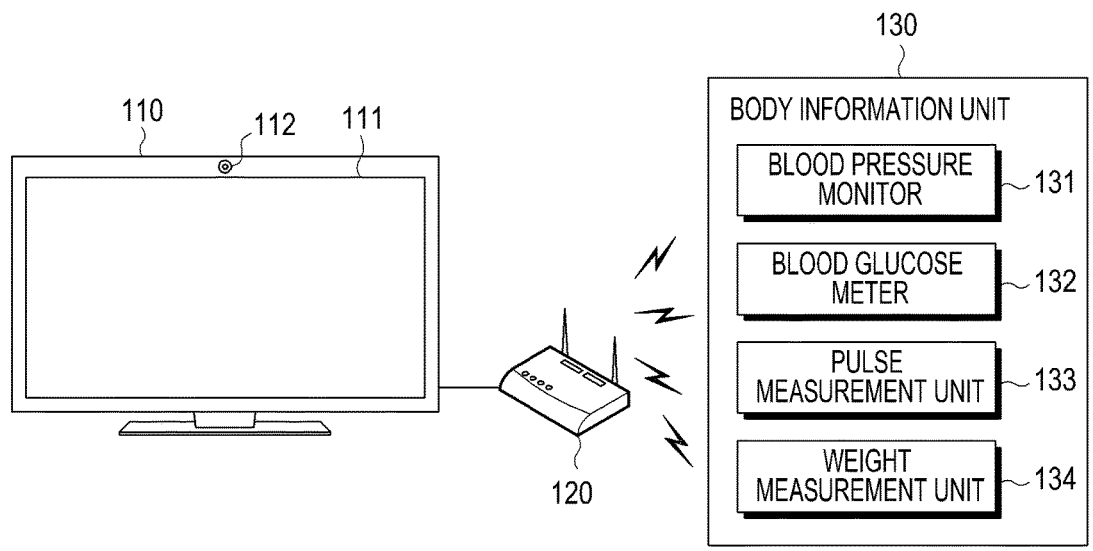
FIG. 1 is a block diagram showing a system for providing health content using health information according to an exemplary embodiment of the present disclosure.

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing operations described is an example; however, the sequence of and/or operations is not limited to that set forth herein and may be changed as is known in the art, with the exception of operations necessarily occurring in a particular order. In addition, respective descriptions of well-known functions and constructions may be omitted for increased clarity and conciseness.

Additionally, exemplary embodiments will now be described more fully hereinafter with reference to the accompanying drawings. The exemplary embodiments may, however, be embodied in many different forms and should not be construed as being limited to the embodiments set forth herein. These embodiments are provided so that this disclosure will be thorough and complete and will fully convey the exemplary embodiments to those of ordinary skill in the art. The scope is defined not by the detailed description but by the appended claims. Like numerals denote like elements throughout.

The present disclosure may have various modifications and various exemplary embodiments, among which specific exemplary embodiments will now be described more fully with reference to the accompanying drawings. However, it should be understood that the present disclosure is not limited to the specific exemplary embodiments, but the present disclosure includes all modifications, equivalents, and alternatives within the spirit and the scope of the present disclosure.

Although the terms including an ordinal number such as first, second, etc. can be used for describing various elements, the structural elements are not restricted by the terms. The terms are only used to distinguish one element from another element. For example, without departing from the scope of the present disclosure, a first structural element may be named a second structural element. Similarly, the second structural element also may be named the first structural element. As used herein, the term "and/or" includes any and all combinations of one or more associated items.

The terms used in this application is for the purpose of describing particular exemplary embodiments only and is not intended to limit the disclosure. As used herein, the singular forms are intended to include the plural forms as well, unless the context clearly indicates otherwise. In the description, it should be understood that the terms "include" or "have" indicate existence of a feature, a number, a step, an operation, a structural element, parts, or a combination thereof, and do not previously exclude the existences or probability of addition of one or more another features, numeral, steps, operations, structural elements, parts, or combinations thereof.

Unless defined differently, all terms used herein, which include technical terminologies or scientific terminologies, have the same meaning as that understood by a person skilled in the art to which the present disclosure belongs. It should be interpreted that the terms, which are identical to those defined in general dictionaries, have the meaning identical to that in the context of the related technique. The terms should not be ideally or excessively interpreted as a formal meaning.

Hereinafter, an operation principle of exemplary embodiments of the present disclosure will be described in detail with reference to the accompanying drawings. In the following description of exemplary embodiments of the present disclosure, a detailed description of known functions or configurations incorporated herein will be omitted when it is determined that the detailed description thereof may unnecessarily obscure the subject matter of the present disclosure. The terms which will be described below are terms defined in consideration of the functions in the present disclosure, and may be different according to users, intentions of the users, or customs. Therefore, the definitions of the terms should be determined based on the content throughout the specification.

First, terms to be used in the present disclosure will be defined as follows.

Terminal: All image reproduction devices including TVs, light emitting diode (LED) TVs, liquid crystal display (LCD) TVs, and smart TVs which can perform transmission and reception of data, voice communications, video communications, and Internet connections and display videos, and can also display videos in interiors of buildings.

FIG. 1 is a block diagram showing a system for providing health content using health information according to an exemplary embodiment of the present disclosure.

Referring to FIG. 1, the system includes a terminal 110 for displaying health content to the user or outputting health content through a speaker. The system may also include a body information measurement unit 130 for specifying body information of the user, and a gateway 120 for receiving health information from the body information measurement unit 130, measuring an indoor environment, and transmitting the health information and the indoor environment to the terminal 110.

The terminal 110 receives one or more pieces of health information from the gateway 120, compares preset threshold values for the received one or more pieces of health information, and controls such that health content suitable for users is provided to solve the differences from the threshold values. The terminal 110 outputs health content through at least one of a display and a speaker. The health content may include information through which a body information value of the user contained in the health information reaches a threshold value. For example, the health content may include information through which body information values, such as a blood pressure, a blood sugar, a pulse, a human body fat, a weight, a height, and an organic composite substances due to atopy, asthma, stress, and exhalation reach their threshold values. The user may maintain his or her health in a better state as the body information values reach their threshold values according to the information. The threshold values may be standard threshold values corresponding to a standard body shape, and the body information includes a blood pressure, a blood sugar, a pulse, a human body fat, a weight, an organic composite substance due to atopy, asthma, stress, and exhalation, and a height of the user. According to another exemplary embodiment the threshold values may be selected and stored by a user. Alternatively, the threshold values may be set according to received information from a user's medical professional such as a physician.

The terminal 110 generates and outputs health content including a method of reaching the threshold values for the health information. The generated health content may include at least one of an exercise method, a diet therapy, a game, a recommend sleeping time, ventilation, recommendation of a hospital, and a difference between threshold values. Further, the present disclosure may provide the user with information helpful to the health of the user in the form of specific health information in addition to the methods of improving the user's values to meet the threshold values. The terminal 110 may transmit a controlling signal, such that a difference in a value of the indoor environment including at least one of temperature, humidity, and cleanness and the threshold value may be controlled, to at least one of an air conditioner, a humidifier, and an air cleaner for a period of time set by the user in advance.

The terminal 110 provides the user with health content using indoor environment information and/or outdoor environment information. The terminal 110 may receive or measure indoor environment, and may receive or measure outdoor environment information. The terminal 110 may compare the received indoor environment information with the received outdoor environment, and may output health content suitable for the user according to the comparison result. The health content includes information for solving a difference between the indoor environment and the outdoor environment. The information contained in the content is information provided to allow the user to adapt to the outdoor environment. The indoor environment information includes at least one of temperature, humidity, ultraviolet ray index, or cleanness. The present disclosure includes various factors that influence the health of the user in an interior space of a building in addition to temperature, humidity, ultraviolet ray index, and cleanness. The indoor environment information may be measured by the terminal 110 or may be measured by the gateway 120 connected to the terminal 110 by a wire or wirelessly. If the indoor environment information is measured by the gateway 120, the gateway 120 may transmit the measurement result to the terminal 110 and the terminal 110 may receive the indoor environment information. The terminal 110 may receive standard threshold values for preset temperature, humidity, ultraviolet ray index, and cleanness to compare the indoor environment with the outdoor environment. In this way, the terminal 110 compares at least two of the indoor environment, the outdoor environment, and the standard threshold value. That is, the terminal 110 may compare the indoor environment and the outdoor environment, or the indoor environment and the standard threshold value, and may compare the indoor environment, the outdoor environment, and the standard threshold value. The terminal 110 may transmit health content to the portable terminal of the user. This allows the user to determine whether the standard threshold value or the outdoor environment value is selected. The terminal 110 may include at least one camera 112 on an outer surface thereof, and may detect a motion or a momentum of a person within an angle of view of the camera 112.

The gateway 120 may be connected to the terminal 110 by a wire or wirelessly, and may be connected to at least one body measurement unit 130 by a wire or wirelessly. The gateway 120 may receive values measured by measurement units for measuring body information of the user, may store the measured values, or transmit the measured values to the terminal 110. The gateway 120 may measure an indoor environment. The indoor environment information includes at least one of indoor temperature, humidity, ultraviolet ray index, and cleanness. The present disclosure includes various factors that influence the health of the user in the interior of a building in addition to temperature, humidity, ultraviolet ray index, and cleanliness.

The body information measurement unit 130 is adapted to measure body information of the user, and may include a height measurement unit and a body temperature measurement unit, as well as a blood pressure monitor 131, a blood glucose meter 132, a pulse measurement unit 133, and a weight measurement unit 134. The body information measurement unit 130 may include various measurement units for measuring factors that influence health of the user, and may perform various measurements that influence the health of the user according to a peripheral environment (for example, temperature, humidity, ultraviolet ray index, and cleanness). The measurement units may include transmission modules for transmitting the measurement results to at least one of the terminal 110 and the gateway 120.

Figure 2:
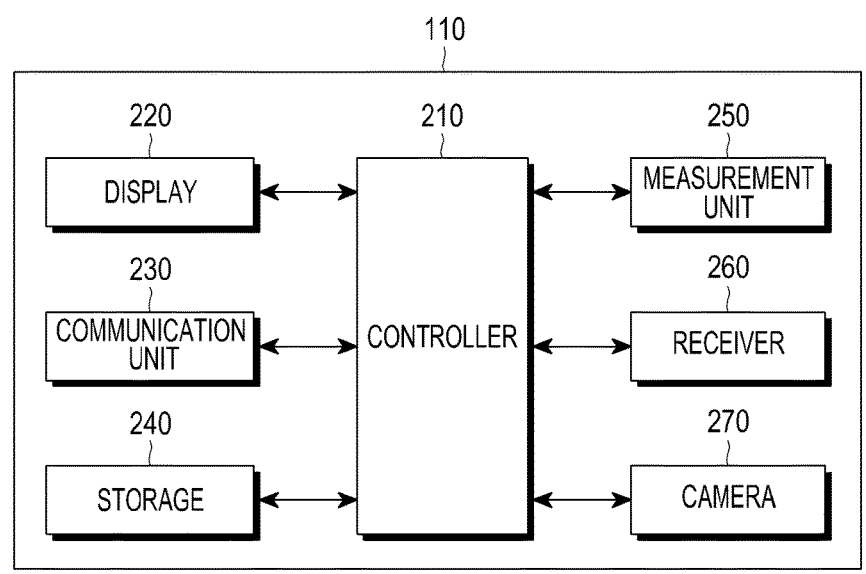
FIG. 2 is a block diagram of a terminal for providing health content according to an exemplary embodiment of the present disclosure.

FIG. 2 is a block diagram of a terminal for providing health content according to an exemplary embodiment of the present disclosure.

Referring to FIG. 2, the terminal 110 for providing health content, according to an exemplary embodiment of the present disclosure, may include any image reproduction devices including TVs, LED TVs, LCD TVs, and smart TVs which can perform transmission and reception of data, voice communications, video communications, and Internet connections and display videos, for example, displaying videos from the interiors of buildings.

The terminal 110 includes a receiver 260 for receiving outdoor environment information from the gateway 120 or through the Internet, a measurement unit 250 for measuring an indoor environment, and a communication unit 230 provided with at least one module for receiving outdoor environment information and various content that may be provided to the user from a server through the gateway 120 and/or Internet. The terminal 110 also includes a controller 210 for comparing at least two of an indoor environment, an outdoor environment, and a threshold value, receiving health content through an external communication network or generating health content according to the comparison result and controlling an overall operation of the terminal 110. Additionally, the terminal 110 may include a storage 240 for storing outdoor environment information received through the receiver 260, indoor environment information measured by the measurement unit 250, and health content that may be provided for a blood pressure, a blood sugar, a pulse, a body fat, a weight, an organic composite substance due to atopy, asthma, stress, and exhalation, and a height of the user included in the environment information, a display 220 for displaying the received or generated health content on a screen, and a camera 270 for capturing a movement or motion of the user to calculate a calorie consumed due to the movement of the user.

The display 220 displays information for generating health content generated by the controller 210 or health content received through the communication unit 230. The health content includes various types of information through which body information values of the user included in the health information received through the receiver 260 reaches a standard threshold value corresponding to a standard body shape.

The display 220, which may include a touchscreen, may receive at least one touch through a user's body (for example, a finger including a thumb) or a touchable input unit (for example, a stylus pen or an electronic pen). The display 220 may receive a continuous movement of the touch, and may transmit an analog signal or digital signal corresponding to the continuous movement of the input touch to the controller 210.

The display 220 may be implemented in a resistive type, a capacitive type, an infrared type, or an acoustic wave type. Further, the display 220 may include at least two touch screen panels which may detect touches or approaches of a body part of the user and the touchable input unit respectively in order to sequentially or simultaneously receive inputs by the body part of the user and the touchable input unit. The display 220 may display one or more health content. The display 220 may include a plurality of pixels and may display an image through pixels, and may employ a Liquid Crystal Display (LCD), an Organic Light Emitting Diode (OLED), and/or a Light Emitting Diode (LED).

The communication unit 230 may allow the terminal 110 to be connected to at least one of Internet, the gateway 120, and the body information measurement unit 130 through a mobile communication using at least one or a plurality of antennas under the control of the controller 210. The communication unit 230 allows the terminal 110 to be connected to the portable terminal, the gateway 120, the body information measurement unit 130, and a server for providing health content and outdoor environment information. The communication unit 230 may include a short-range communication module or a wireless LAN module, or may include both a short-range communication module and a wireless LAN module. The communication unit 230 may be connected to the Internet in a place in which a wireless Access Point (AP) is installed, under the control of the controller 210. The short-range communication method of the communication unit 230 may include Bluetooth, Infrared Data Association (IrDA), a WiFi-Direct communication, and/or Near Field Communication (NFC). The communication unit 230 may include at least one of a mobile communication module, a wireless LAN module and a short-range communication module according to its performance.

The storage 240 may store at least one piece of health information, outdoor environment information, indoor environment information, and a difference value between the information. The storage 240 may also store various applications or programs for allowing the user to manage his or her health. The storage 240 may store at least one of an exercise method, a diet therapy, a game, a recommend sleeping time, ventilation, recommendation of a hospital, and a difference between threshold values for a blood pressure, a blood sugar, a pulse, a human body fat, a weight, an organic composite substance due to atopy, asthma, stress, and exhalation, and a height of the user included in the health information to generate health content. The storage 240 may further store information that recommends wearing at least one of specific clothing items, a sunscreen agent, ultraviolet ray shielding glasses, and a mask, and an additional function by which at least one of temperature, humidity, ultraviolet ray index, and cleanliness included in indoor environment information reaches at least one of temperature, humidity, ultraviolet ray index, or cleanliness in order to generate health content. The storage 240 may store health content for users, and may store various types of information including health content received through an external communication network.

The storage 240 may store a signal or data input and output to correspond to an operation of the display 220, the communication unit 230, the measurement unit 250, the receiver 260, and the camera 270 under the control of the controller 210. The storage 240 may store control programs for control of the terminal 110 or the controller 210 and applications for generating health content. The storage 240 may include a memory card (for example, an SD card or a memory stick) mounted to an ROM or a RAM in the controller 210 or the terminal 110, and may include a nonvolatile memory, a volatile memory, a Hard Disk Drive (HDD) or a Solid State Drive (SSD).

Further, the storage 240 can store images for providing applications having various functions such as a navigation, a video call, a game and an alarm application based on time and Graphical User Interfaces (GUIs) related to the applications, databases, or data related to a method of processing user information, a document, a touch input, background images (menu screen, standby screen and the like) required for driving the portable terminal 110, operating programs, and/or images photographed by the camera module 270. The storage 240 may be a machine (for example, computer)-readable medium. The term "machine-readable medium" may be defined as a medium capable of providing data to the machine so that the machine performs a specific function. The machine readable medium may be a storage medium. The storage 240 may include a non-volatile medium and a volatile medium. All of these media should be of a type that allows commands transferred by the media to be detected by a physical mechanism through which the machine reads the commands.

The measurement unit 250 includes at least one sensor for detecting a state of the user or an indoor environmental state. The measurement unit 250 may measure at least one of a blood pressure, a blood sugar, a pulse, a human body fat, a weight, an organic composite substance due to atopy, asthma, stress, and exhalation, and a height of the user, or may measure at least one of an indoor environment including at least one of temperature, humidity, ultraviolet ray index, and cleanness. The measurement unit 250 may measure an indoor environment, as well as body information influencing the health of the user, in addition to the above-described body information or an indoor environment. The measurement unit 250 may include a proximity sensor for detecting an approach of the user to the terminal 110, an illumination intensity sensor for detecting an amount of light around the terminal 110, a geomagnetic sensor for detecting a point of compass using a geomagnetic field, a gravity sensor for detecting a direction of the gravity, and an altimeter for measuring the atmospheric pressure to detect an altitude. At least one sensor may detect the state, and may generate a signal corresponding to the detection to transmit the generated signal to the controller 210. The measurement unit 250 may measure at least one of a blood pressure, a blood sugar, a pulse, a human body fat, a weight, an organic composite substance due to atopy, asthma, stress, and exhalation, and a height of the user, or may measure at least one of an indoor environment including at least one of temperature, humidity, ultraviolet ray index, or cleanliness. The present disclosure may measure various factors that can influence the health of the user in addition to the above-described ones, and the measurement result may be stored in the storage 240. The measurement unit 250 may be added or deleted according to a performance or structure of the terminal 110.

The receiver 260 may receive the body information measured by the body information measurement unit 130 through the gateway 120. The receiver 260 may directly receive the body information measured by the body information measurement unit 130. The receiver 260 may receive body information of the user from at least one of the gateway 120 and the body information measurement unit 130, and may be connected to the gateway 120 and the body information measurement unit 130 by a wire or wirelessly.

The camera 270 may be provided outside the terminal 110, and capture a movement or motion of the user to transmit the movement of the user to the controller 210. A consumed calorie is calculated by capturing, or photographing, and analyzing the movement or motion of the user. The camera 270 may include at least one camera for photographing a still image or a video under the control of the controller 210. The camera 270 may include, in addition to an image sensor, at least one of a body tube for performing a zoom-in/zoom-out operation to photograph a subject, a motor for controlling a movement of the body tube, a flash for providing an auxiliary light source for photographing a subject. At least one camera provided in the camera 270 may convert an optical signal input (or photographed) through a lens system into an electrical image signal and output the electrical image signal to the controller 210, and the controller 210 may calculate a calorie consumed by the user through a video photographed by the at least one camera.

The controller 210 controls an overall operation of the display 220, the communication unit 230, the storage 240, the measurement unit 250, the receiver 260, and the camera 270 provided in the terminal 110 for providing health content. When receiving one or more pieces of health information from the gateway 120, the controller 210 may compare preset threshold values with the received one or more pieces of health information, and the controller 210 may then provide control such that health content suitable for users are provided to solve the differences from the threshold values. The controller 210 outputs health content through at least one of a display and a speaker. The health content includes information through which a living body information value of the user contained in the health information reaches a threshold value. The threshold values are standard threshold values corresponding to a standard body shape, and the living body information includes a blood pressure, a blood sugar, a pulse, a human body fat, a weight, an organic composite substance due to atopy, asthma, stress, exhalation, and a height of the user. Alternatively, the threshold values may be tailored to the user by the user or a third party. The controller 210 generates and outputs health content including a method of reaching the threshold values for the health information. The generated health content include at least one of an exercise method, a diet therapy, a game, a recommend sleeping time, ventilation, recommendation of a hospital, and a difference between threshold values. The controller 210 transmits a signal controlling such that a difference a value of the indoor environment including at least one of a temperature, a humidity, a cleanliness, and the threshold value to at least one of an air conditioner, a humidifier, and an air cleaner for a period of time set by the user in advance.

If receiving indoor environment information and outdoor environment information, the controller 210 compares the received indoor environment information with the received outdoor environment information, and outputs health content suitable for the user according to the comparison result. The output health content includes information for solving a difference between the indoor environment and the outdoor environment. The information contained in the content is information provided to allow the user to adapt to the outdoor environment. The indoor environment information includes at least one of temperature, humidity, ultraviolet ray index, and cleanness. The indoor environment information may be measured by the measurement unit 250 or may be measured by the gateway 120 connected to the terminal 110 wired or wirelessly. If the indoor environment information is measured by the gateway 120, the gateway 120 may transmit the measurement result to the terminal 110 and the terminal 110 may receive the indoor environment information. The terminal 110 may receive standard threshold values for preset temperature, humidity, ultraviolet ray index, and cleanliness to compare the indoor environment with the outdoor environment. In this way, the controller 210 compares at least two of the indoor environment, the outdoor environment, and the standard threshold value. That is, the controller 210 may compare the indoor environment and the outdoor environment or the indoor environment and the standard threshold value, and may compare the indoor environment, the outdoor environment, and the standard threshold value. The controller 210 may analyze a video photographed by the camera 270 in order to recognize a movement or momentum of the user, and may calculate a calorie consumed per unit time through the intensity of the motion. The calculated calorie may be used for generation of health content. The controller 210 may transmit the health content to the portable terminal of the user through the communication unit 230.

Figure 3:
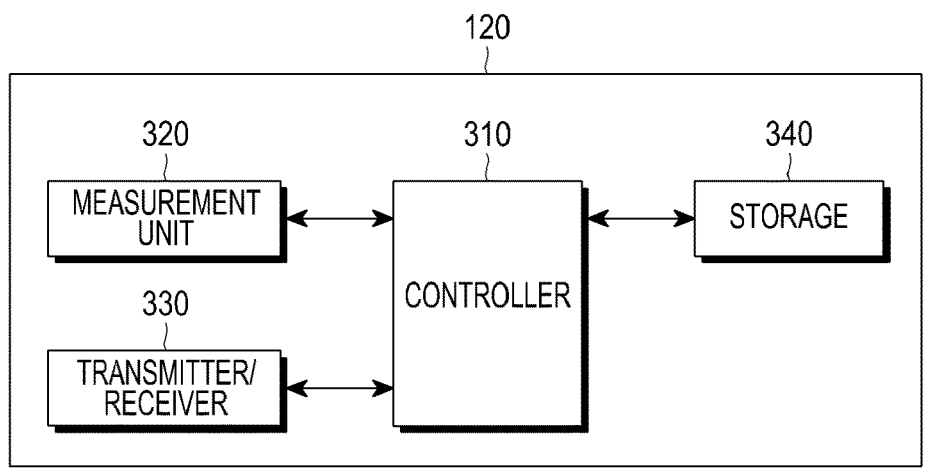
FIG. 3 is a block diagram of a gateway for measuring an indoor environment according to an exemplary embodiment of the present disclosure.

FIG. 3 is a block diagram of a gateway for measuring an indoor environment according to an exemplary embodiment of the present disclosure.

Referring to FIG. 3, the gateway 120 for measuring an indoor environment according to an exemplary embodiment of the present disclosure may transmit and receive data between the terminal 110 and the body information measurement unit 130, may transmit and receive data through connection to an Internet network, and may measure an indoor environment.

The gateway 120 may include a measurement unit 320, a transmitter/receiver 330, a storage 340, and a controller 310.

The measurement unit 320 may include at least one sensor for detecting an indoor environment state. The measurement unit 320 may measure an indoor environment including at least one of a temperature, a humidity, an ultraviolet ray index, and a cleanness of an interior of a building. The measurement unit 320 may measure various environments that influence the health of the user in addition to the above-described temperature, humidity, ultraviolet ray index, and cleanliness of the interior of the building. The measurement unit 320 may include a proximity sensor for detecting an approach of the user to the gateway 120, an illumination intensity sensor for detecting an amount of light around the gateway 120, and a geomagnetic sensor for detecting a point of compass using a geomagnetic field. At least one sensor may detect the indoor environment state, and may generate a signal corresponding to the detection to transmit the generated signal to the controller 310. The measurement unit 320 may measure an indoor environment including at least one of a temperature, a humidity, an ultraviolet ray index, and a cleanness of an interior of a building. The present disclosure may measure various factors that can influence the health of the user in addition to the above-described ones, and the measurement result may be stored in the storage 340 and may be transmitted to the terminal 110 through the transmitter/receiver 330. The measurement unit 320 may be added or deleted according to a performance or structure of the gateway 120.

The transmitter/receiver 330 may be connected to the terminal 110 and the body information measurement unit 130 through a mobile communication using at least one or a plurality of antennas under the control of the controller 310. The transmitter/receiver 330 may be connected to the body information measurement unit 130, and a server for providing health content and outdoor environment information. The transmitter/receiver 330 may include a short-range communication module or a wireless LAN module, or may include both a short-range communication module and a wireless LAN module. The transmitter/receiver 330 may be connected to the Internet in a place in which a wireless Access Point (AP) is installed, under the control of the controller 310. The short-range communication method of the transmitter/receiver 330 may include Bluetooth, Infrared Data Association (IrDA), a WiFi-Direct communication, and Near Field Communication (NFC).

The storage 340 may store at least one piece of health information, outdoor environment information, indoor environment information, and a difference value between the information. The storage 340 may store at least one of an exercise method, a diet therapy, a game, a recommend sleeping time, ventilation, recommendation of a hospital, and a difference between threshold values for a blood pressure, a blood sugar, a pulse, a human body fat, a weight, an organic composite substance due to atopy, asthma, stress, and exhalation, and the height of the user included in the health information in order to generate health content. The storage 340 may store information that recommends at least one of wearing of clothes, a sunscreen agent, ultraviolet ray shielding glasses, and a mask, and an additional function by which at least one of temperature, humidity, ultraviolet ray index, and cleanliness included in indoor environment information reaches at least one of temperature, humidity, ultraviolet ray index, and cleanness to generate health content. The storage 340 may store health content for users, and may store various types of information including health content received through an external communication network.

The controller 310 controls an overall operation of the measurement unit 320, the transmitter/receiver 330, and the storage 340 provided in the gateway 120. If receiving at least one piece of health information from the body information measurement unit 130, the controller may store the received at least one piece of health information or transmit it to the terminal 110. The controller 310 may analyze body information measured by the at least one body information measurement unit 130. The health information is used in health content generated by the terminal 110. The controller 310 transmits a signal controlling such that a difference a value of the indoor environment including at least one of a temperature, a humidity, and a cleanliness and the threshold value to at least one of an air conditioner, a humidifier, and an air cleaner for a period of time set by the user in advance.

If measuring indoor environment information or receiving outdoor environment information, the controller 210 may compare the received indoor environment information with the received outdoor environment information, or transmit the comparison result to the terminal 110. The indoor environment information includes at least one of temperature, humidity, ultraviolet ray index, and cleanliness. The indoor environment information may be measured by the measurement unit 320 or the terminal 110. If the indoor environment information is measured by the measurement unit 320, the controller 310 may transmit the measurement result to the terminal 110 and the terminal 110 may receive the indoor environment information. The gateway 120 may receive standard threshold values for preset temperature, humidity, ultraviolet ray index, and cleanliness from a server existing outside the terminal through an Internet network to compare the indoor environment with the outdoor environment. The controller 210 may transmit the health content received from the terminal 110 to the portable terminal of the user through the communication unit 330.

Figure 4:
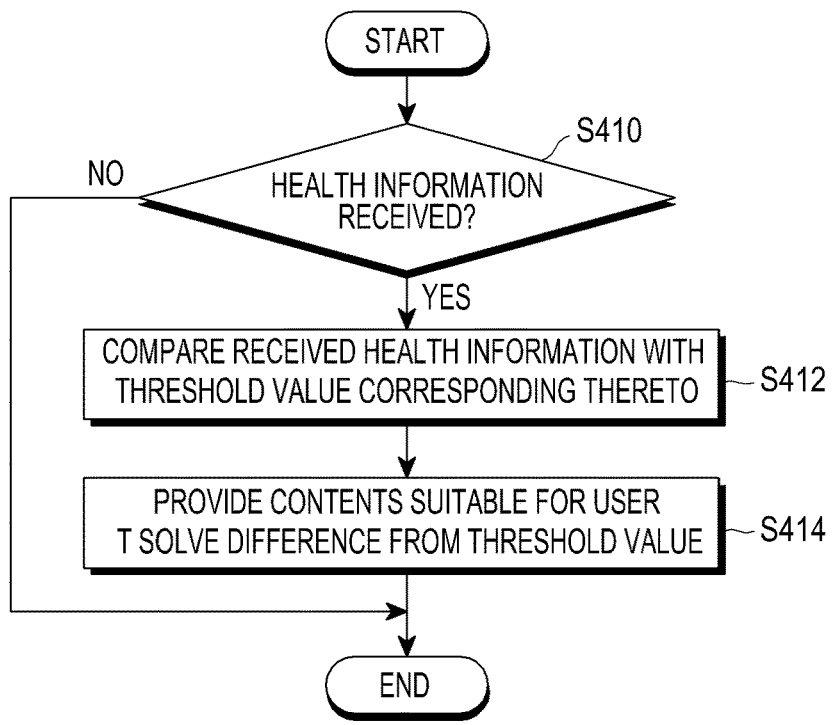
FIG. 4 is a flowchart showing a method of providing health content using health information of a terminal according to an exemplary embodiment of the present disclosure.

FIG. 4 is a flowchart showing a method of providing health content using health information of a terminal according to an exemplary embodiment of the present disclosure.

Hereinafter, a method of providing health content using health information of a terminal according to an exemplary embodiment of the present disclosure will be described in detail.

When health information is received, the received health information is compared with a threshold value corresponding thereto (S410 and S412). When at least one piece of health information is received, the health information is compared with a preset threshold value for the health information. The health information may be received through the gateway 120 connected to the terminal 110 by wire or wirelessly, or may be received through the body information measurement unit 130. The health information includes body information of the user, and the body information includes a blood pressure, a blood sugar, a pulse, a human body fat, a weight, an organic composite substance due to atopy, asthma, stress, and exhalation, and the height of the user. The body information may include a concentration of an organic composite substance measured through exhalation of a person. The organic composite gas includes at least one of acetone, ammonia, nitrogen monoxide, and toluene. The threshold values are standard threshold values corresponding to a standard body shape, and the body information may be set to different values for a blood pressure, a blood sugar, a pulse, a human body fat, a weight, an organic composite substance due to atopy, asthma, stress, and exhalation, and a height of the user. For example, a threshold value for a standard blood pressure corresponding to a blood pressure of the body information is about 120 mmHg for a contraction period and about 80 mmHg for a relaxation period. The threshold value for a standard blood sugar corresponding to a blood sugar is shown in Table 1.

TABLE 1

| Diagnosis | Fasting blood sugar value | Blood sugar value 2 hours after meals | Glycosylated hemoglobin value |
|---|---|---|---|
| Normal | 70~110 mg/dl | 70~140 mg/dl | 4.0~5.7% |
| Step before | 110~125 mg/dl | 70~140 mg/dl | 5.8~6.4% |

TABLE 1-continued

| Diagnosis | Fasting blood sugar value | Blood sugar value 2 hours after meals | Glycosylated hemoglobin value |
|---|---|---|---|
| glycosuria, preliminary glycosuria (Fasting blood sugar disorder) | | | |
| Step before glycosuria, preliminary glycosuria (Impaired glucose tolerance) | 110~125 mg/dl | 140~200 mg/dl | 5.8~6.4% |
| Determination of glycosuria | 126 mg/dl or higher | 200 mg/dl or higher | 6.5% or higher |

In Table 1, if a fasting blood sugar exceeds 126 mg/dl two or times or more, it may be determined to be glycosuria, and if a value two hours after a grape sugar test is 200 mg/dl or more, it may be determined to be glycosuria. If the value arbitrarily measured, regardless of meals, is 200 mg/dl while one has a glycosuria symptom, it may be determined to be glycosuria.

A threshold value for a standard pulse corresponding to a pulse of body information is 100 to 140 for infants, 80 to 90 for children, 60 to 80 young adults and middle-aged people, and 60 to 70 for old people in a stable state. A standard human body fat corresponding to a human body fat of body information is as Table 2.

TABLE 2

| | | Fat percentage (%) | | |
|---|---|---|---|---|
| Classification | | Normal | Slightly fat | Fat |
| Male | Less than 30 | 14-20 | 21-25 | 26 or more |
| | 30 or more | 17-23 | 24-28 | 29 or more |
| Female | Less than 30 | 17-24 | 25-29 | 30 or more |
| | 30 or more | 20-27 | 28-32 | 33 or more |

Further, the present disclosure may determine a disease suffered by a user through exhalations of the user. The present disclosure may determine whether the disease suffered by the user is glycosuria, nephropathy, asthma, lung cancer, or stomach cancer through exhalations.

The exhalation discharged when the user breathes may include acetone, ammonia, nitric oxide, and toluene. Acetone of a healthy person is less than 900 ppb (parts per billion), ammonia of a healthy person is 29 to 688 ppb, and nitrogen monoxide of a healthy person is 6.7 to 16.2 ppb. However, acetone of an unhealthy person is less than 1800 ppb or higher, ammonia of an unhealthy person is 820 to 14700 ppb, and nitrogen monoxide of an unhealthy person is 34.7 to 51.1 ppb. It may be determined whether the user is suffering a certain disease through a reference value for a chemical element, and the present disclosure can provide information (for example, ventilation or recommendation of a hospital) recommendable for the disease.

When health information including at least one of blood pressure, blood sugar, pulse, human body fat, atopy, asthma, stress, height, various diseases, and weight is received, the received at least one piece of health information is compared with the threshold value. When health information including a chemical substance included in exhalation is received, the present disclosure compares the received at least one piece of health information with the threshold value.

Further, content suitable for the user is provided to solve the difference from the threshold value (S414). In operation S412, health content suitable for the user are generated to solve the difference from the threshold value according to the comparison result, and the generated health content are provided. The health content may include helpful information provided to the user such that body information value of the user included in the health information reaches the threshold value. For example, the health content may include an exercise method, a diet therapy, a game, ventilation, recommendation of a hospital, and a recommend sleeping time for health information. The health content may be displayed on the display or may be vocally output through the speaker. The health content may be output through both the display and the speaker. The health content may be transmitted to the portable terminal of the user to allow the user to receive the health content without limitation in place. The controller 210 transmits a signal controlling such that a difference a value of the indoor environment including at least one of a temperature, a humidity, and a cleanliness and the threshold value to at least one of an air conditioner, a humidifier, and an air cleaner for a period of time set by the user in advance. The air conditioner, the humidifier, and the air cleaner may include a reception module for receiving the signal.

Figure 5:
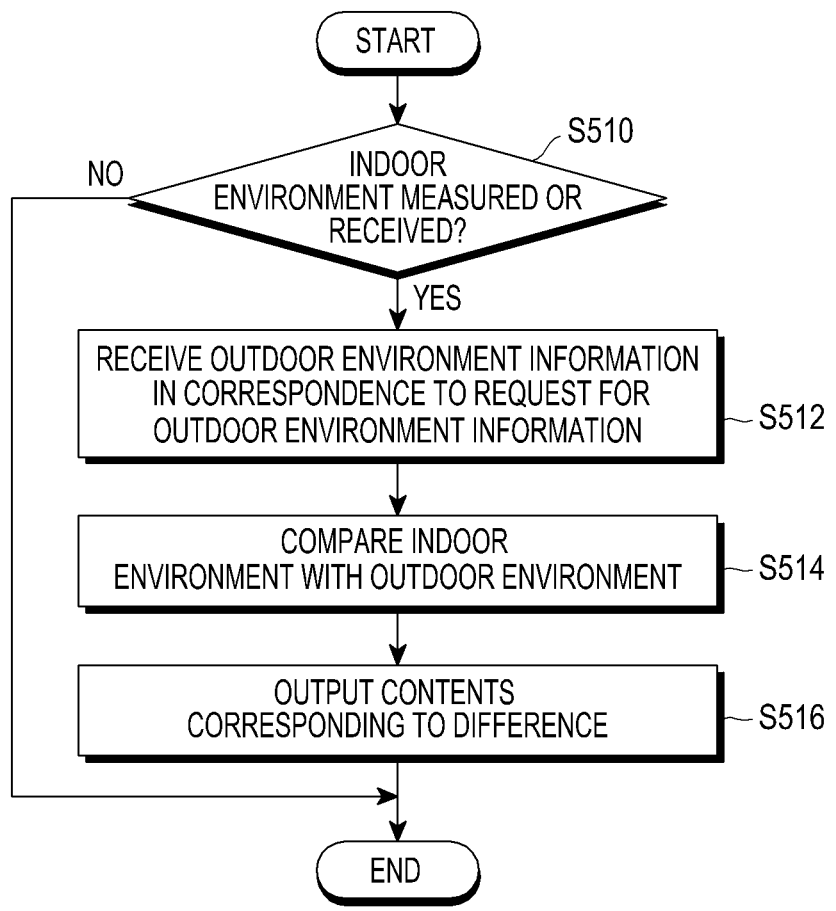
FIG. 5 is a flowchart showing a process of comparing an indoor environment with an outdoor environment and providing health content according to an exemplary embodiment of the present disclosure.

FIG. 5 is a flowchart showing a process of comparing an indoor environment with an outdoor environment and providing health content according to an exemplary embodiment of the present disclosure.

Hereinafter, a process of comparing an indoor environment with an outdoor environment and providing health content according to an exemplary embodiment of the present disclosure will be described with reference to FIG. 5.

When an indoor environment is measured or received, outdoor environment information is received to correspond to a request for outdoor environment information (S510, S512). The terminal 110 may receive a standard threshold value. The standard threshold value is a standard value of a temperature, a humidity, an ultraviolet ray index, or a cleanness corresponding to a season or a date. The terminal 110 may determine how an indoor or outdoor environment is different from the standard threshold value through the indoor environment, the outdoor environment, and the standard threshold value. The indoor environment may be measured through at least one sensor provided in the terminal 110 or may be measured by the gateway 120 connected to the terminal 110 wired or wirelessly. The indoor environment information includes at least one of temperature, humidity, ultraviolet ray index, and cleanness. The gateway 120 may be connected to the terminal 110 wired or wirelessly, and may be connected to at least one living body measurement device 130 wired or wirelessly. The gateway 120 may receive values measured by measurement devices for measuring body information of the user, or may store the measured values or transmit the measured values to the terminal 110. The gateway 120 may measure an indoor environment. The terminal 110 requests outdoor environment information from a server for periodically or non-periodically providing outdoor environment information. The outdoor environment information includes at least one of outdoor temperature, humidity, ultraviolet ray index, and cleanliness as outdoor environment information. The server may be a meteorological administration server for providing environment information such as an outdoor temperature, a humidity, an ultraviolet ray index, and a cleanliness, or may be a server of a portal business such as Daum or Naver for providing environment information.

The outdoor environment information and the indoor environment information received in operation S512 are compared (S514). The terminal 110 may determine how an indoor or outdoor environment is different from the standard threshold value through at least two of the indoor environment, the outdoor environment, and the standard threshold value. The terminal 110 receives indoor environment information and outdoor environment information, and compares the received indoor environment information with the received outdoor environment information. The comparisons may be performed for a temperature, a humidity, an ultraviolet ray index, and a cleanliness included in the environment information.

Content corresponding to the comparison result are output (S516). The terminal 110 outputs health content suitable for the user according to the comparison result. The indoor environment information may be measured by the terminal 110 or may be measured by the gateway 120 connected to the terminal 110 wired or wirelessly. The output health content includes information for solving a difference between the indoor environment and the outdoor environment. The information contained in the content is information provided to allow the user to adapt to the outdoor environment. The storage 240 may store information that recommends at least one of: the wearing of particular clothing items, a sunscreen agent, ultraviolet ray shielding glasses, and a mask, and an additional function by which at least one of temperature, humidity, ultraviolet ray index, and cleanliness included in indoor environment information reaches at least one of temperature, humidity, ultraviolet ray index, and cleanness. In addition, the health content may include different types of information according to the health state of the user, and may further include various types of information received through an external communication network. The terminal 110 may transmit health content to the portable terminal of the user. The content may be output through the display 220, and may be output through a speaker.

It may be appreciated that the exemplary embodiments of the present disclosure may be implemented in software, hardware, or a combination thereof. Any such software may be stored, for example, in a volatile or non-volatile storage device such as a ROM, a memory such as a RAM, a memory chip, a memory device, or a memory IC, or a recordable optical or magnetic medium such as a CD, a DVD, a magnetic disk, or a magnetic tape, regardless of its ability to be erased or its ability to be re-recorded. It can be also appreciated that the memory included in the portable terminal is one example of machine-readable devices suitable for storing a program including instructions that are executed by a processor device to thereby implement exemplary embodiments of the present disclosure. Accordingly, the present disclosure includes a program that includes a code for implementing an apparatus or a method defined in any claim in the present specification and a machine-readable storage medium that stores such a program. Further, the program may be electronically transferred by a predetermined medium such as a communication signal transferred through a wired or wireless connection, and the present disclosure appropriately includes equivalents of the program.

Further, the terminal can receive the program from a program providing apparatus connected to the device wirelessly or through a wire and store the received program. The program providing apparatus may include a memory for storing a program containing instructions for allowing the terminal to perform the health content providing method and information required for the health content providing method, a communication unit for performing wired or wireless communication with the terminal, and a controller for transmitting the corresponding program to the host apparatus according to a request of the terminal or automatically.

While exemplary embodiments have been described with respect to a limited number of embodiments, those skilled in the art, having the benefit of this disclosure, will appreciate that other embodiments can be devised which do not depart from the scope as disclosed herein. Accordingly, the scope should be limited only by the attached claims.

What is claimed is:

1. A method for providing health data in an electronic device, the method comprising:
   receiving, by a communication interface of the electronic device, first biometric values of a user and environment information related to the user;
   determining, by a processor of the electronic device, a difference between the first biometric values and second biometric values of a standard body shape;
   generating, by the processor, a control signal for changing at least one environment value measured in an interior, based on the environment information, wherein the at least one environment value includes a temperature, a humidity, or an ultraviolet ray index;
   displaying, by the processor, health data on a display of the electronic device by guiding, to the user, an exercise method, a game, a recommended sleeping time, ventilation information, or information about a recommended hospital for decreasing the difference; and
   transmitting, by the communication interface, the control signal to at least one appliance in the interior such that an operation for changing the temperature, the humidity or the ultraviolet ray index is executed by the at least one appliance in response to the control signal.

2. The method of claim 1, wherein the health data is further outputted through a speaker of the electronic device.

3. The method of claim 1, wherein the first biometric values comprise a blood pressure value, a blood sugar value, a pulse value, a human body fat value, a weight value, an atopy state, an asthma state, a stress state, an organic composite substance value due to and exhalation of the user, or a height of the user.

4. The method of claim 1, wherein the at least one appliance includes an air conditioner, a humidifier or an air cleaner.

5. An electronic device for providing health data, the electronic device comprising:
   a display;
   a communication interface configured to receive first biometric values of a user and environment information related to the user; and
   a processor configured to:
      determine a difference between the first biometric values and second biometric values of a standard body shape,
      generate a control signal for changing at least one environment value measured in an interior, based on the environment information, wherein the at least one environment value includes a temperature, a humidity, or an ultraviolet ray index,
      control the display to display health data by guiding, to a user of the electronic device, an exercise method, a game, a recommended sleeping time, ventilation information, or information about a recommended hospital for decreasing the difference, and
      control the communication interface to transmit the control signal to at least one appliance in the interior such that an operation for changing the temperature, the humidity or the ultraviolet ray index is executed by the at least one appliance in response to the control signal.

6. The electronic device of claim 5, wherein the processor is further configured to: transmit the health data to a portable terminal, a gateway, one or more sensors for measuring biometric values of the user, or a server.

7. The electronic device of claim 5, further comprising:
   a camera configured to detect a movement of the user, wherein the processor is further configured to calculate a calorie consumed through the movement of the user.

8. The electronic device of claim 5, the health data is further outputted through a speaker of the electronic device.

9. The electronic device of claim 5, wherein the at least one appliance includes an air conditioner, a humidifier or an air cleaner.

* * * * *